United States Patent [19]
Hofmann et al.

[11] Patent Number: 5,951,323
[45] Date of Patent: Sep. 14, 1999

[54] CONNECTOR FOR SEMICONDUCTOR MICROELECTRODES AND FLEXIBLE WIRING

[75] Inventors: Ulrich G. Hofmann; David T. Kewley; James M. Bower, all of Pasadena, Calif.

[73] Assignee: California Institute of Technology, Pasadena, Calif.

[21] Appl. No.: 08/924,394

[22] Filed: Sep. 5, 1997

[51] Int. Cl.⁶ .................................................. H01R 11/18
[52] U.S. Cl. .......................................... 439/482; 324/72.5
[58] Field of Search .................................. 324/72.5, 754, 324/761; 439/482

[56] References Cited

U.S. PATENT DOCUMENTS

| | | | |
|---|---|---|---|
| 4,811,081 | 3/1989 | Lyden | 357/80 |
| 5,012,186 | 4/1991 | Gleason | 439/482 |
| 5,061,892 | 10/1991 | O'Hara et al. | 439/482 |
| 5,150,969 | 9/1992 | Goldberg et al. | 374/128 |
| 5,164,595 | 11/1992 | Musselman et al. | 250/306 |
| 5,517,752 | 5/1996 | Sakata et al. | 29/832 |
| 5,745,624 | 4/1998 | Chan et al. | 385/91 |

OTHER PUBLICATIONS

Brochure, *Heat Seal Connectors*, 3M, 1995, 2 pages.
Brochure, *Southwall Altair M Transparent Conductive Film*, Southwall Technologies, Inc., 1995, 2 pages.
Brochure, *ZEBRA W Series Elastomeric Connectors*, Fujipoly America Corp., 1996, 6 pages.
Center for Integrated Sensors and Circuits, *Micromachined Stimulating Electrodes*, Quarterly Report #5, Jan. 1997, 24 pages.
Kewley, et al., *Plasma–Etched Neural Probes*, Sensors and Actuators A (Physical), A58(1):27, 1997.

*Primary Examiner*—Khiem Nguyen
*Attorney, Agent, or Firm*—Fish & Richardson P.C.

[57] ABSTRACT

A fixture for carrying a neural probe. The fixture has a base with opposite forward and rear ends, the rear end having an engagement feature for engaging a micropositioner and the forward end having a receiving feature for receiving the semiconductor substrate base of the probe.

11 Claims, 4 Drawing Sheets

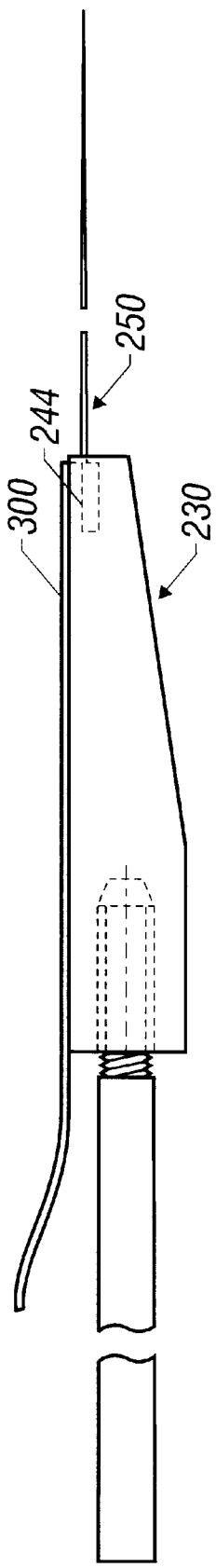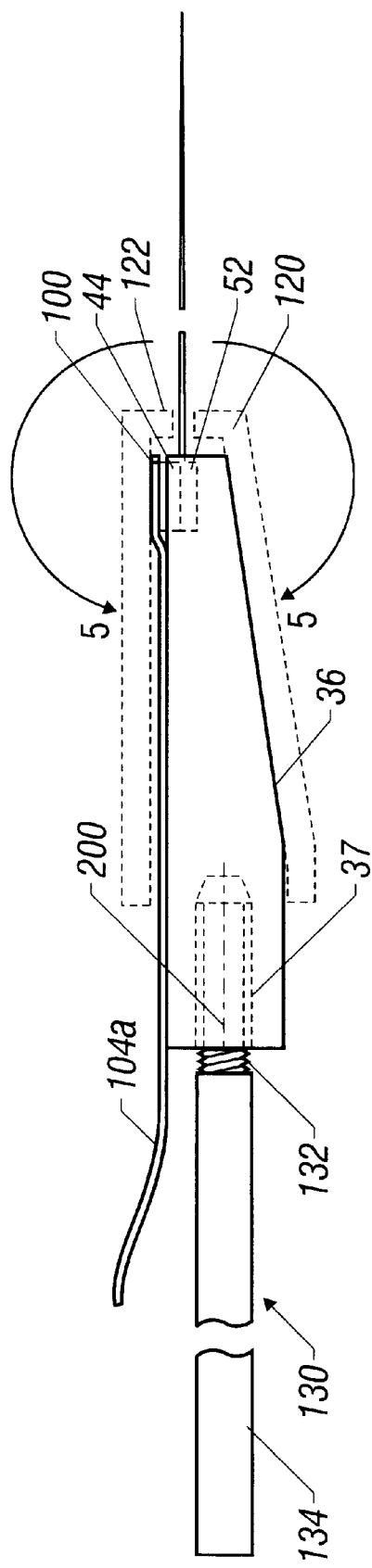

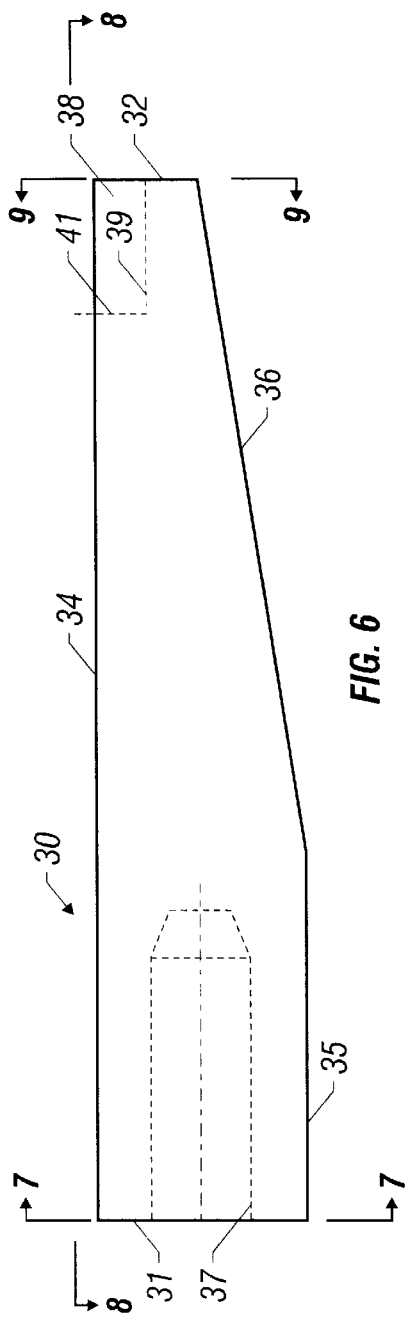
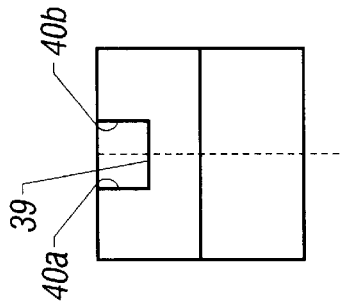
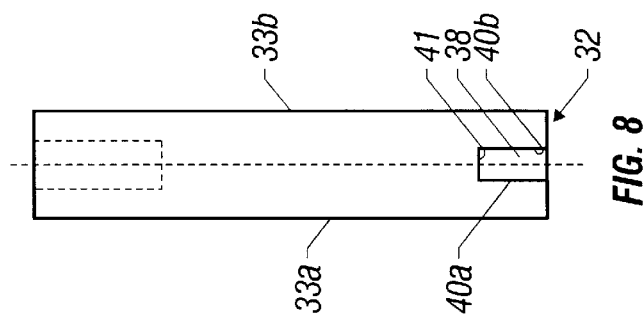
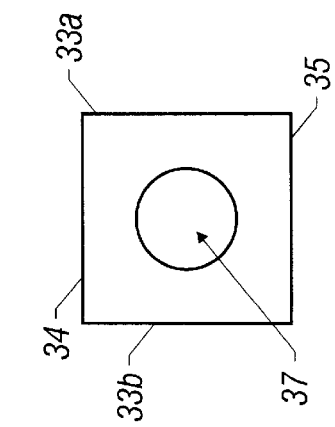

ps://patents.google.com/patent/US5951323

CONNECTOR FOR SEMICONDUCTOR MICROELECTRODES AND FLEXIBLE WIRING

STATEMENT AS TO FEDERALLY SPONSORED RESEARCH

The U.S. Government has certain rights in this invention pursuant to Grant No. BIR-9513903 awarded by the National Science Foundation.

BACKGROUND

1. Technical Field

This invention relates to biomedical probes, and more particularly to neural probes of the type having an electrode extending distally from a semiconductor base.

2. Background Information

The use of semiconductor-based neural probes has begun to replace the use of prior wire bundle probe systems. In a broad form, the probe elements in such systems comprise a semiconductor substrate base with one or more electrodes. More precisely, such a probe may have electrode-bearing shafts extending distally from the forward edge of the semiconductor base.

As shown in FIG. 1, the probe element 10 is preferably held by a micropositioner 12 which facilitates the precise introduction of the electrode-bearing shaft 14 into a desired area. Shaft 14 is usually introduced into a neural mass 16, such as a target brain region under study in the laboratory. A processing unit 18 is provided to receive electrical signals from and provide electrical signals to the probe element.

To provide mechanical connection between the probe element 10 and micropositioner 12, the probe base is adhered to the surface of a circuit board 20 adjacent its forward end. Electrical communication between the probe element 10 and processing unit 18 is effected by wire bonding techniques which are used to connect contact pads on the probe base to associated contacts on the circuit board. A cable 22 may then be provided to connect the circuit board to the processing equipment. This completes the electrical path from the electrodes to the equipment. The probe base may be encapsulated by applying a drop of encapsulation material atop the base so as to protect the wiring and further secure the base to the circuit board. The circuit board is also attached to the micropositioner 12 such as by mounting the circuit board on a base 24 which is connected to the micropositioner by means of a shaft 26.

Such systems may be unduly cumbersome. Additionally, the encapsulation material which is applied to cover the base may bend the electrode-bearing shafts as it hardens. This can create further alignment problems. Alignment is critical for accurate and precise insertion and guidance of the electrodes to their targets. The shafts should all be parallel to each other and parallel to an insertion axis of the micropositioner.

Accordingly, it is desirable to provide a compact and robust system for providing precise alignment of the electrode-bearing shafts of a probe with the axis of a micropositioner.

SUMMARY

The present invention facilitates the provision of a probe fixture which can hold the base of a probe element registered in a precise predetermined orientation to allow the precise positioning and insertion of the probe electrodes into a neural mass under study. To establish electrical communication between the probe and associated processing equipment, a flexible conductor strip may be utilized. To minimize physical deformation and interference with the probe, the flexible conductor strip may be placed in a parallel facing orientation to a contact-bearing surface of the base. An anisotropic connective medium may establish electrical contact between conductors in the flexible conductor and associated contacts on the base. Exemplary anisotropic connective media include an elastomeric matrix with an embedded array of conductive wires which may be held under compression such as by an internally tapered shoe which encompasses the correspondingly tapered fixture at least at the base of the probe element. An alternative anisotropic connective medium may include an anisotropic conducting adhesive which may adhere the flexible conductor to the substrate base.

Registration of the base of the probe element may be achieved by providing the fixture with registration features comprising a recess extending inward from a front end of the fixture and having a flat bottom and flat sides for mating with a flat bottom and flat sides of the base of the probe.

The assembly is secured to a micropositioner. The fixture may be provided with a longitudinal threaded bore oriented substantially parallel to the electrodes of the probe. A threaded shaft may be mated with the threaded bore.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 is a partial semi-schematic and cut-away view of a neural probe assembly according to principles of the invention.

FIG. 6 is a side view of a probe fixture of the assembly of FIG. 4.

FIG. 7 is a rear view of the fixture of FIG. 6 taken along line 7—7.

FIG. 8 is a top view of the fixture of FIG. 6 taken along line 8—8.

FIG. 9 is a front view of the fixture of FIG. 6 taken along line 9—9.

FIG. 10 is a partial semi-schematic and cut-away view of a second probe assembly according to principles of the invention.

Like reference numbers and designations in the various drawings indicate like elements.

DETAILED DESCRIPTION

Figure 2:
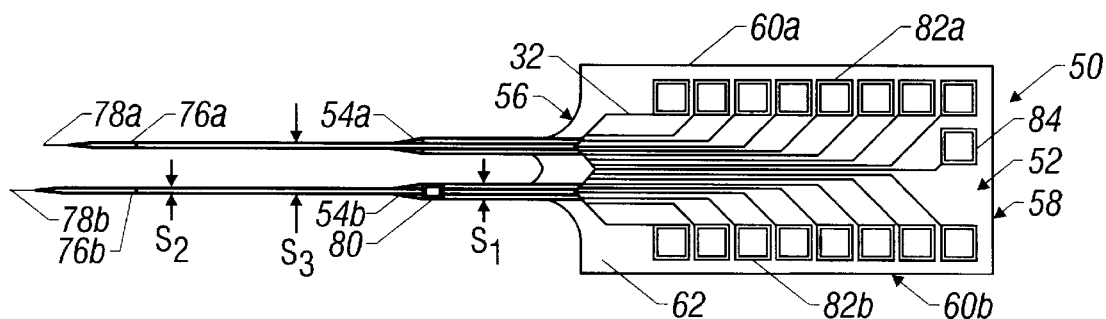
FIG. 2 is a top view of a semiconductor-based neural probe element.
Figure 5:
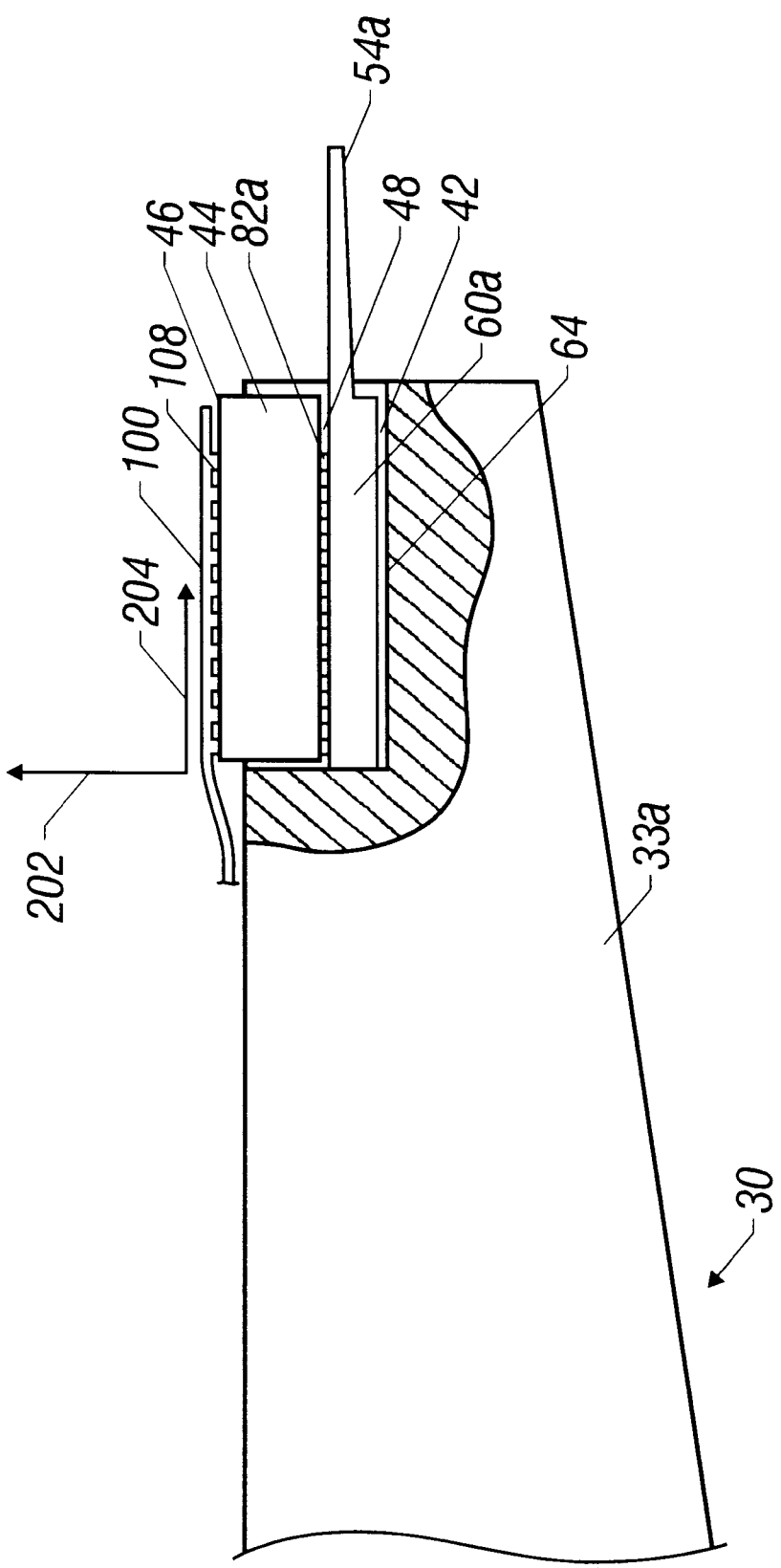
FIG. 5 is an enlarged view of a portion of the probe assembly of FIG. 4.

As shown in FIG. 2, a neural probe element 50 is formed of a semiconductor substrate having a base section 52 and a pair of thin elongate shafts 54a and 54b, extending forward from a forward edge 56 of the base 52. The base 52 has a straight flat rear edge 58 and respective straight flat right and left edges 60a and 60b, respectively. The base has a substantially planar upper face 62 and lower face 64 (FIG. 5). By any number of conventional semiconductor device fabrication techniques, the probe element is provided with a linear array of electrodes 76a and 76b, slightly recessed from the tips 78a and 78b of the right and left probe shafts 54a and 54b, respectively. A reference electrode 80 is located at an intermediate location along one of the shafts. The electrodes 76a and 76b and 80 are each connected to a metal contact 82a and 82b and 84, respectively, on the upper surface of the base by a conductive interconnect trace 82. Each interconnect trace is insulated from the other interconnect traces. If desired, various circuit elements may be included on the base. In an exemplary embodiment, the probe element is formed from a p-type semiconductor wafer having a thickness of 25 μm. The edges are machined to provide a substantially uniform base width of 1.30 millimeter and a base length of approximately 2.5 millimeter. The probe shafts are approximately 3 mm in length and are formed by chemical etching of the semiconductor substrate. In the exemplary embodiment, the probes have a trunk area of width $s_1$ extending approximately ⅓ of their length and tapering to a narrow portion of width $S_2$ for substantially the remainder, ending in a sharp tip. In the exemplary embodiment, the shafts are separated by distance $S_3$ and they have slightly offset lengths. Exemplary values for $S_1$, $S_2$ and $S_3$ are 0.09, 0.040 mm and 0.3 millimeters respectively.

Figure 3:
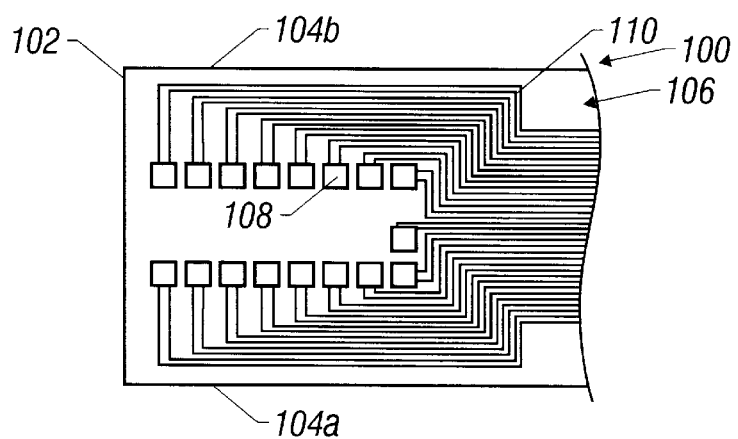
FIG. 3 is a partial semi-schematic view of the underside of a distal end of a flexible conductor.

As shown in FIG. 3, a flexible connector strip 100 is formed with a forward edge 102 and right and left edges 104a and 104b, respectively. The strip has an underside 106 onto which metallic contacts 108 are provided by conventional means. Each contact 108 is connected to a conductive interconnect trace 110 which extends toward the rear end of the strip. The interconnect traces 110 are also formed by conventional means, and are insulated from each other.

An exemplary flexible conductor strip is formed of polyester film onto which iridium tin oxide interconnect traces are sputtered and gold contacts applied. Via any number of conventional flexible film photolithographic techniques, similar structures may be prepared. Exemplary strip material is available from Southwall Technologies, Inc. under the trademark ALTAIR™.

As shown in FIGS. 4–9, a first embodiment of a fixture 30 for carrying the probe element 50 is formed as an elongate piece extending from a generally planar rear face 31 at the rear end of the fixture to a generally flat front face 32 at the front end of the fixture. Symmetric right and left faces 33a and 33b, respectively, run perpendicularly between the rear and front faces. The fixture comprises a generally planar top 34 connecting and perpendicular to the front rear and side faces. The fixture further comprises a bottom having a planar rear portion 35 extending perpendicular to and forward from the rear face and joining a planar forward portion 36 at a slight angle to the front and rear faces so as to provide a general rear to front taper. A threaded cylindrical bore 37 extends longitudinally forward from the rear face 31 and has a central longitudinal axis 200 parallel to the forward direction 204.

A recess 38 is open at the upper front edge of the fixture to the front face 32 and top face 34. The recess extends rearward and downward from those faces, respectively. The recess has a flat substantially planar rectangular bottom 39 parallel to the top 34 of the fixture and, more importantly, to the bore 37. The recess has flat planar right and left sides 40a and 40b respectively extending from the bottom 39 to the fixture top 34 and joining the front face 32 of the fixture. The recess further has a flat rear side 41 also extending from the recess bottom 39 to the fixture top 34.

In an exemplary embodiment, the fixture is machined from an acetal resin and formed to be 20 millimeters long, 4 millimeters high and 4 millimeters wide. The front face 32 is 2 millimeters high and the rear section 35 of the fixture bottom being approximately 27 millimeters in length so that the tapered portion of the fixture along the front portion 36 of the fixture bottom is at an approximate 9° taper. Further, the recess 38 is substantially a uniform 1.0 millimeter deep, 2.7 millimeters long and approximately 1.29–1.34 millimeters wide. The bore 37 is approximately 1.9 millimeters in diameter.

As shown in FIG. 4 and in greater detail in FIG. 5, the assembly may be prepared by first applying an optional adhesive layer 42 either to the bottom 39 of the recess or the bottom surface 39, of the base. The base is then inserted into the recess, left and right edges of the base engaging left and right faces of the recess, the rear edge of the base engaging the rear face of the recess and the lower face of the base engaging the bottom of the recess so as to register the base in a predetermined parallel alignment relative to the axis 200.

An anisotropic connective medium 44 is placed atop the upper surface of the base so as to engage contacts 82a and 82b and 84. The anisotropic connective medium 44 acts as a conductor along a single coordinate axis and as an insulator along the two orthogonal axes. In the exemplary embodiment, the anisotropic connective medium is oriented so that the medium is conductive in the vertical direction 202 and the medium is nonconductive transverse to the vertical direction.

The respective contacts of the base and connector strip are positioned so that each contact on the base is aligned, along the conductive direction of the anisotropic connective medium, with the associated contact on the conductor strip. This establishes direct conductive paths between the associated contacts with no significant crosstalk.

In the exemplary embodiment, the connective medium is formed as a rectangular block of an elastomeric matrix with an embedded array of metal wires extending vertically within the matrix to provide conductive paths through the matrix. A suitable material featuring a silicone matrix is sold under the trademark ZEBRA™ by Fujiopoly America Corp. The flexible connector strip 100 is then placed atop the anisotropic connective medium 44 so that each contact 108 of the strip 100 is immediately above a corresponding contact 82a, 82b and 84 of the probe element, the lower face of the strip and upper face of the base in parallel facing spaced-apart relation separated by the anisotropic connective medium 44. The contacts 108 of the flexible conductor strip engage the upper face 46 of the connective medium 44 and the contacts 82a, 82b and 84 of the base engage the lower face 48 of the connective medium 44 so as to establish electrical contact between the conductors in the flexible conductor strip and the associated contacts on the base.

As shown in FIG. 5, one way of maintaining compressive engagement of the anisotropic connective medium 44 between the flexible conductor strip 100 and probe base 52 is by the application of a shoe 120 to the fixture. The shoe comprises a sleeve having a rear to forward taper substantially matching that of the fixture and an aperture 122 through which the probe shafts may pass without interference. The shoe encompasses at least the portions of the fixture and base at the connective medium 44. A positive friction engagement is obtained by extending the shoe 120 substantially along the length of the forward section 36 of the fixture.

Figure 1:
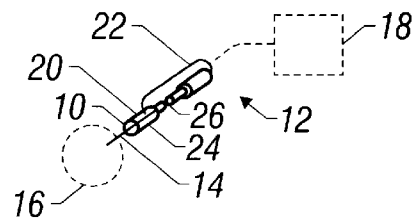
FIG. 1 is a partial semi-schematic view of a neural probe and associated equipment.

As further shown in FIG. 4, the fixture is provided with an elongate cylindrical shaft 130 having a threaded front end 132 mated with the threaded bore 37 and a rear end 134 for engaging micropositioner 12 of FIG. 1.

FIG. 10 shows an alternate embodiment in which the probe assembly includes a fixture 230, a probe element 250 and a flexible connector strip 300 which may be otherwise similar to those of FIG. 4. However, an alternate anisotropic connective medium is provided by a conductive adhesive layer 244. An exemplary material is available from Minnesota Mining and Manufacturing Co. as "3M Heat Seal Connector".

A number of embodiments of the present invention have been described. Nevertheless, it will be understood that various modifications may be made without departing from the spirit and scope of the invention. For example, the number and geometry of the electrodes and their shafts are influenced by the constraints of the particular experiment and desires of the experimenter. A variety of registration features other than the basic right parallel walled recess may be used. Accordingly, other embodiments are within the scope of the following claims.

What is claimed is:

1. A neural probe assembly, securable to a micropositioner for delivering electrical signals from a neural mass to remote equipment, the assembly comprising:
   a probe element having a semiconductor substrate base and an elongate probe shaft extending forward from the base;
   a fixture having parts for capturing and registering the base in precise orientation and having a securing feature for securing the assembly to the micropositioner;
   a flexible conductor for providing electrical communication between the probe element and the remote equipment, the flexible conductor having a forward end portion in substantially parallel spaced-apart relation with an upper surface of the substrate base of the probe element; and
   an anisotropic connective medium establishing electrical contact between conductors in said flexible conductor and associated contacts on said base.

2. The probe assembly of claim 1 wherein the securing feature comprises a threaded bore oriented substantially parallel to the elongate probe shaft.

3. The probe assembly of claim 2 wherein the securing feature further comprises a threaded shaft mated with the threaded bore.

4. The probe assembly of claim 1 wherein the fixture comprises a capturing recess extending inward from a front end of the fixture, the recess having registration features for mating with registration features of the substrate base for registering the base and fixture in precise orientation.

5. The probe assembly of claim 4 wherein the registration features of the recess comprise a flat bottom and flat sides of the capturing recess and wherein the registration features of the substrate base comprise a flat bottom and flat sides of the base configured to simultaneously engage the flat bottom and flat sides of the recess.

6. The probe assembly of claim 1 wherein said probe element comprises two elongate probe shafts in parallel spaced-apart relation.

7. The probe assembly of claim 1 further comprising an element holding the anisotropic connective medium under compression.

8. The probe assembly of claim 1 wherein the fixture has a rear to front taper, which assembly further comprises a shoe having at least an internal rear to front taper encompassing at least a portion of the fixture and base at the anisotropic connective medium and holding the anisotropic connective medium in compression between the flexible conductor and the base.

9. The probe assembly of claim 8 wherein the anisotropic connective medium comprises an elastomeric matrix with an embedded array of metal wires.

10. The probe assembly of claim 1 wherein the securing feature comprises an elongate shaft extending rearward from the fixture.

11. The probe assembly of claim 1 wherein the anisotropic connective medium adheres the flexible conductor to the substrate base.

* * * * *